(12) United States Patent
Roberts

(10) Patent No.: US 8,141,442 B2
(45) Date of Patent: Mar. 27, 2012

(54) PIPE SCANNER

(75) Inventor: Douglas J. Roberts, Willington, CT (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 435 days.

(21) Appl. No.: 12/434,717

(22) Filed: May 4, 2009

(65) Prior Publication Data
US 2010/0275694 A1 Nov. 4, 2010

(51) Int. Cl.
*G01N 19/00* (2006.01)
(52) U.S. Cl. ...................................................... 73/865.8
(58) Field of Classification Search .......................... None
See application file for complete search history.

(56) References Cited

U.S. PATENT DOCUMENTS

| | | | | |
|---|---|---|---|---|
| 2,427,129 A | * | 9/1947 | Fields | 15/88 |
| 3,445,655 A | | 5/1969 | Curry | |
| 3,921,440 A | * | 11/1975 | Toth | 73/622 |
| 4,331,034 A | | 5/1982 | Takeda et al. | |
| 4,531,413 A | * | 7/1985 | Tsuchita et al. | 73/637 |
| 5,069,234 A | * | 12/1991 | Nielsen | 134/113 |
| 2005/0041775 A1 | * | 2/2005 | Batzinger et al. | 378/59 |
| 2009/0120215 A1 | * | 5/2009 | Jacobson et al. | 73/865.8 |

FOREIGN PATENT DOCUMENTS

JP 2001-194352 * 7/2001

* cited by examiner

*Primary Examiner* — Robert R Raevis

(57) ABSTRACT

A pipe scanner for non-destructively scanning an extended length of the circumference of a pipe along an axial dimension. The pipe scanner includes a collar sized to fit around the outer circumference of the pipe. Wheels supported on the collar ride on the surface of the pipe while maintaining a space between the inner surface of the collar and the outer surface of the pipe. A track extends circumferentially around the collar for guiding a circumferential drive unit that rides on the track and carries a non-destructive sensor for monitoring the surface of the pipe as the circumferential drive unit moves around the track. An axial drive unit is connected to the collar, having a plurality of circumferentially spaced drive wheels in contact with the pipe for moving the collar along the extended length.

19 Claims, 6 Drawing Sheets

PIPE SCANNER

BACKGROUND OF THE INVENTION

1. Field of the Invention

This invention pertains generally to pipe scanners for the non-destructive examination of piping and, more particularly, to such scanners that can continuously scan the 360° circumference of a pipe over an extended length.

2. Description of Related Art

A leak in the Alaskan oil pipeline caused a major environmental concern that necessitated the shutdown of the Alaskan oil pipeline for a considerable period. As a result, a scanner was developed to continuously monitor the condition of the pipeline to avoid a similar catastrophe in the future. The scanner developed for the Alaskan Pipeline was designed for a 34 inch (86.36 cm.) diameter pipe and only would scan the lower half of the pipe. Typically, pipe scanners are limited to a 24 inch (60.96 cm.) stroke, i.e., the distance they can travel along a pipe without human intervention. After completing a 24 inch (60.96 cm.) stroke they would need to be manually relocated on the pipe to the next 24 inch (60.96 cm.) interval. That interval is even less when compensating for overlap to guarantee 100% coverage. The design of the Alaskan Pipeline scanner was a good first step to avoid future environmental contamination, however, a more versatile design is desired that can scan the 360° circumference of the pipe over an extended length without human intervention. Desirably, such a scanner should be capable of traveling axially along the pipe at relatively high speeds without a need for relocation except when negotiating a riser or vertical support member, which in the case of the Alaskan Pipeline are approximately 60 feet apart.

SUMMARY OF THE INVENTION

This invention achieves the foregoing objectives by providing a scanner capable of traveling axially along a pipe at approximately 20 inches (50.8 cm.) per second and that does not need to be removed from the pipe except when negotiating a riser or vertical support member. The circumferential scanning drive is capable of moving at a speed of approximately 10 inches (25.4 cm.) per second. The circumferential drive is mounted on a circular collar, appropriate to the pipe diameter being scanned. The collar is, in turn, connected to an axial drive that rides on the pipe's surface.

More particularly, the pipe scanner of this invention basically includes a collar sized to fit around the outer circumference of the pipe with wheels supported by the collar oriented to travel axially on an outer surface of the pipe along its extended length. A track on an outer surface of the collar extends circumferentially, substantially around the collar. A circumferential drive travels over the track in either a clockwise or counterclockwise direction around the outer circumference of the collar. A non-destructive sensor is supported on the circumferential drive, for monitoring the surface of the pipe. In addition, an axial drive is connected to the collar for moving the collar longitudinally along the pipe. The axial drive has a drive surface that rides on the outer surface of the pipe for moving the collar along the extended length.

In one embodiment, the drive surface of the axial drive is at least one wheel and, preferably, the wheel is magnetized to gain traction on ferrous piping. Preferably, the drive surface comprises at least two wheels with each wheel spaced from the other around the circumference of the pipe. In the embodiment in which the axial drive has at least two drive surfaces that are circumferentially spaced from each other, a first motor operates a first of the drive surfaces and a second motor operates a second of the drive surfaces and the first and second motors are synchronized. Optionally, a wheel support assembly is attached at one end to the first motor and at a second end around the pipe to the second motor with an idler wheel extending off the wheel support assembly toward the pipe, substantially midway between the first and second motors. Desirably, means are provided for remotely moving the idler wheel towards and away from engagement with the pipe. Preferably, the wheel support assembly includes a wheel housing, attachment arms that extend out from either side of the wheel housing and attachment brackets that extend from the distal ends of the attachment arms, wherein the attachment arms are coupled to the wheel housing with a quick disconnect. The quick disconnect enables the attachment arms to be easily interchanged with attachment arms of another configuration to accommodate different diameter piping.

In still another embodiment, the circumferential drive can travel 360° or more around the outer circumference of the collar, wherein the distance the circumferential drive moves around the circumference, the direction of such moves and the timing of such moves are all programmable and the circumferential drive can travel in either a forward or reverse circumferential direction. Furthermore, in this latter embodiment, the distance the axial drive moves the collar, the direction of such moves and the timing of such moves are all programmable. Additionally, the programming of the circumferential drive is independent of the programming of the axial drive.

In still another embodiment, the non-destructive sensor can be remotely positioned. Furthermore, the wheels supported by the collar maintain a space between an interior of the collar and the outer surface of the pipe that is sufficient to accommodate angled pipe runs. Preferably, the track on the collar comprises a radially outward raised rib that extends circumferentially, substantially continuously around the collar. In such an arrangement, the circumferential drive includes at least two wheels oriented to run circumferentially and spaced from each other to receive the rib therebetween. The pipe scanner of this invention may also include a support arm that is cantilevered off of the circumferential drive and supports the sensor over the pipe with the support arm attached to the circumferential drive through a servo positioning joint.

BRIEF DESCRIPTION OF THE DRAWINGS

A further understanding of the invention can be gained from the following description of the preferred embodiment when read in conjunction with accompanying drawings in which.

DESCRIPTION OF THE PREFERRED EMBODIMENT

Figure 1:
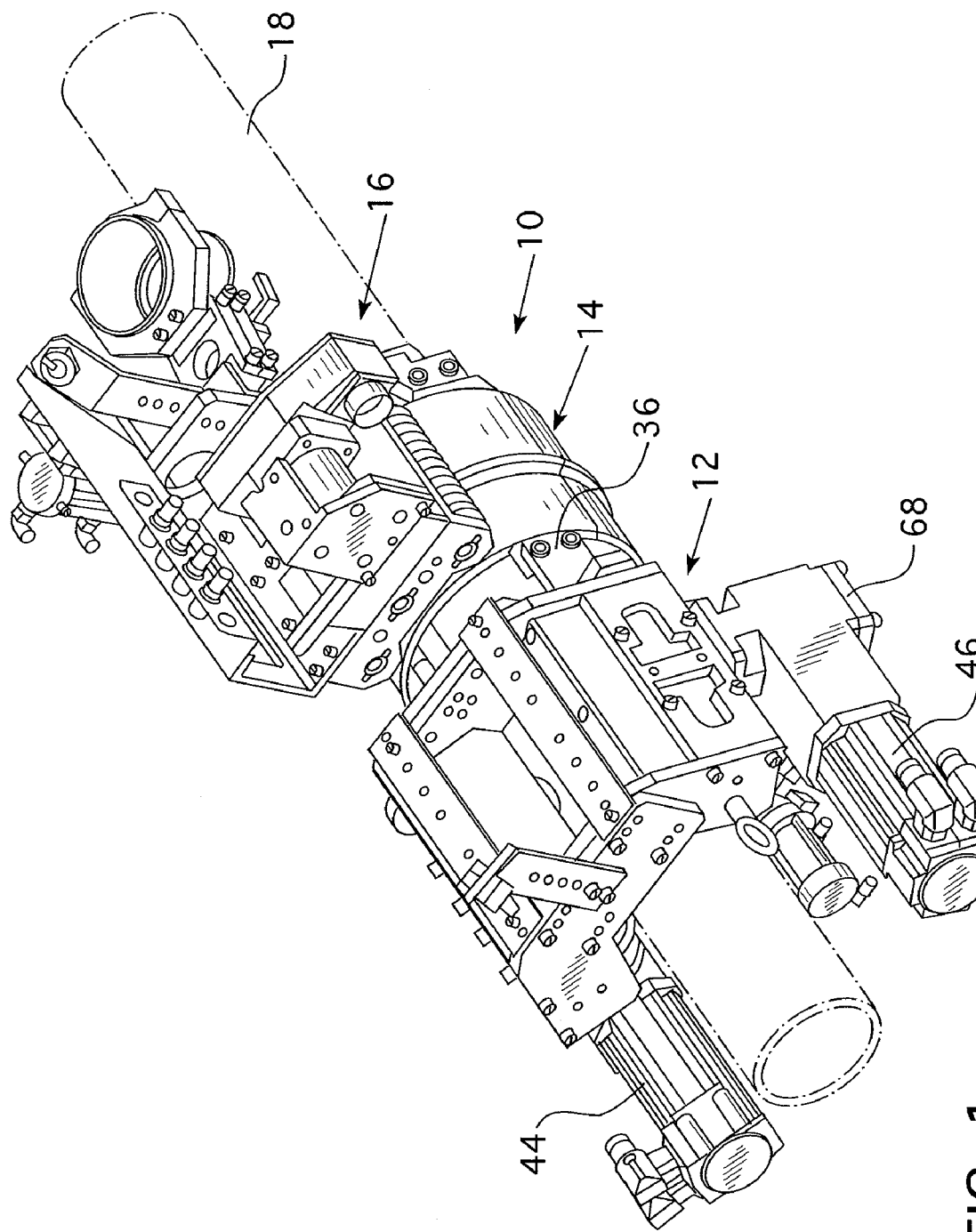
FIG. 1 is an isometric view of the scanning system of this invention positioned over a pipe which is shown in phantom.

Typically, pipe scanners with a an axial drive are supported by a fixed arm on which they move in the axial direction. The fixed arm is cantilevered over the pipe parallel with the axis of the pipe and generally limits the axial movement of the scanner to approximately a 24 inch (61 cm.) stroke. In such an arrangement, after completing a 360° circumferential scan, the scanner has to be manually relocated on the pipe to the next 24 inch (61 cm.) interval (less when compensating for overlap to guarantee 100% coverage). The scanner of this invention overcomes that limitation and provides a modular design that can be used on varying sized pipe. The scanner is capable of traveling axially along the pipe at 20 inches (50.8 cm.) per second and does not need to be removed except when negotiating a riser or vertical support member. In the case of the Alaskan Pipeline, the vertical support members may be approximately 60 feet (18.3 m.) apart. Thus, in such an application the scanner of this invention would increase the scanning inspection throughput.

The circumferential drive on the scanning system of this invention includes a commercially available scanner such as the pipe scanner Model 5080/5085 with magnetic wheels available from WesDyne AMDATA, 20 International Drive, Windsor, Conn. 06095. The circumferential drive is capable of moving at a speed of 10 inches (25.4 cm.) per second. The circumferential drive is mounted to a circular collar, appropriate to the pipe diameter being scanned. The circular collar includes support rollers that allow it to be used on angled pipe. The axial drive is driven with two brushless servo motors with magnetic wheels, one on each side of the pipe. The axial drive can also tow alternate inspection equipment such as an array of low frequency eddy current coils, if desired. To facilitate unmanned scanning, the pipe scanner includes forward and aft color cameras and a pneumatically actuated pipe cleaning device. The pipe cleaning device is a steel brush that may be put into contact with the surface of the pipe and driven with the circumferential drive of the scanner. Optionally, a fixed arm cantilevered from the circumferential drive, which supports a sensor for non-destructively examining the pipe surface and the cleaning device, may be replaced with a servo driven arm which may be used to scan an adjacent pipe up to a pipe riser and/or a portion of the riser itself.

Figure 2:
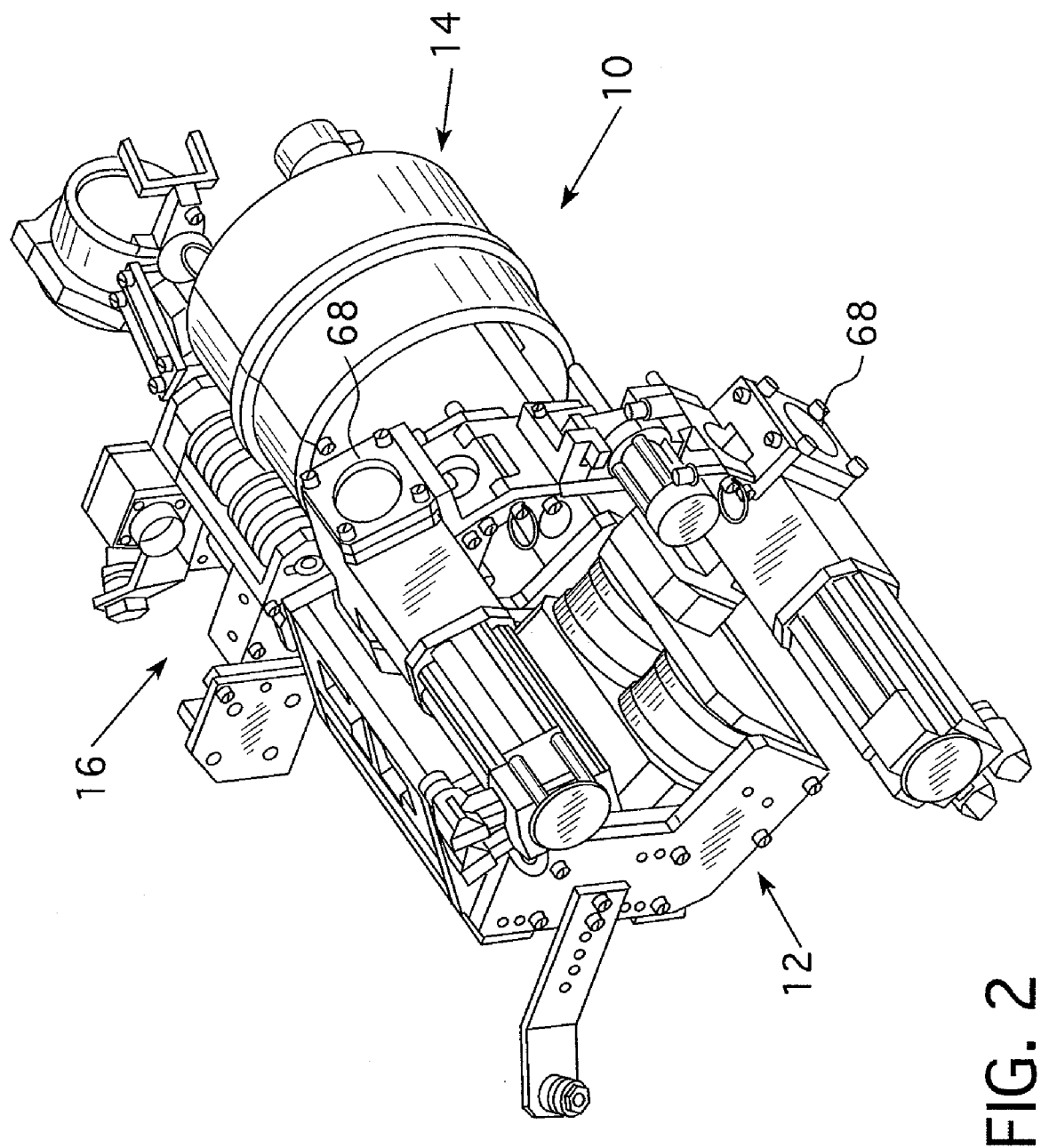
FIG. 2 is an isometric view of the scanning system shown in FIG. 1 rotated approximately a little over 90° in a counter-clockwise direction.

More particularly, the scanner system 10 of this invention is shown in the isometric views illustrated in FIGS. 1 and 2. The scanner system 10 shown in FIG. 1 over pipe 18 illustrated in phantom is shown in FIG. 2 rotated counterclockwise approximately a little more than 90° to reveal some additional features of the invention that are hidden from the view shown in FIG. 1. The scanner system 10 includes, generally, three modular components; an axial drive 12, a collar 14 and a circumferential drive 16.

Figure 3:
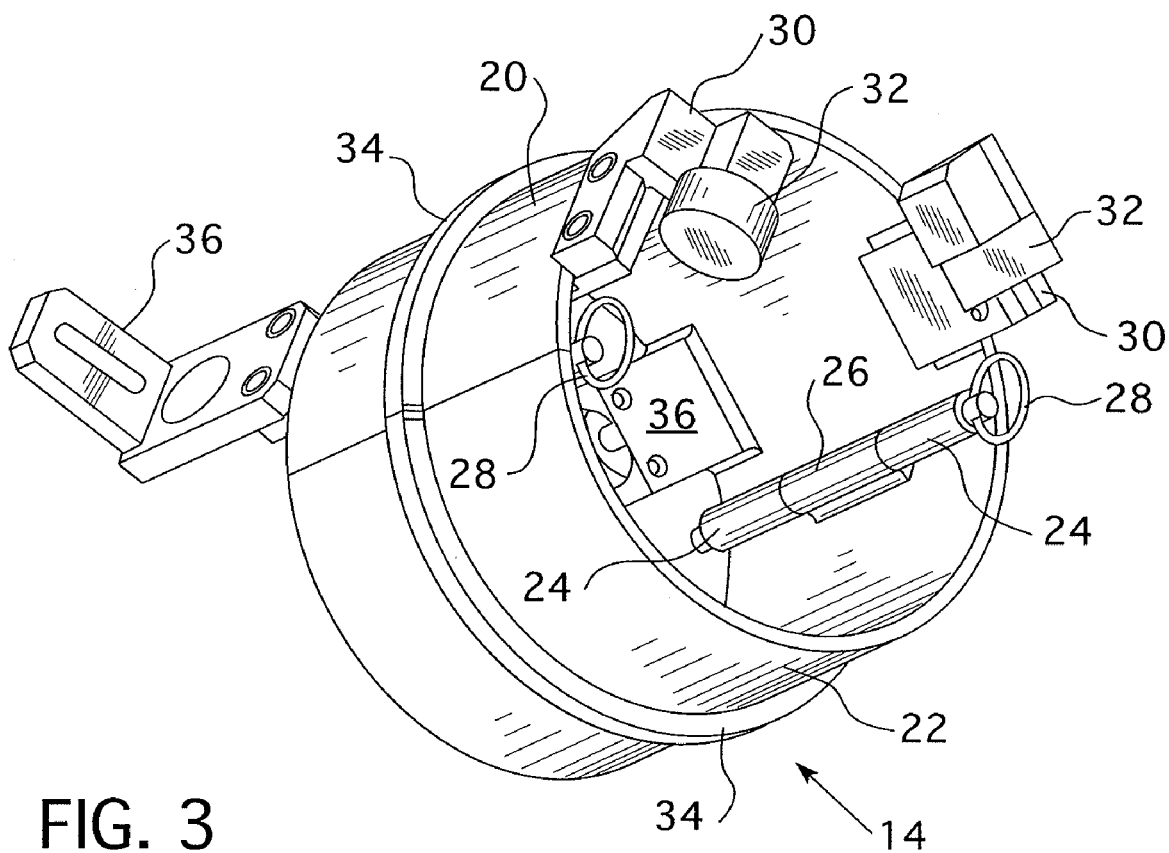
FIG. 3 is a perspective view of the collar assembly of this invention shown in FIGS. 1 and 2.
Figure 4:
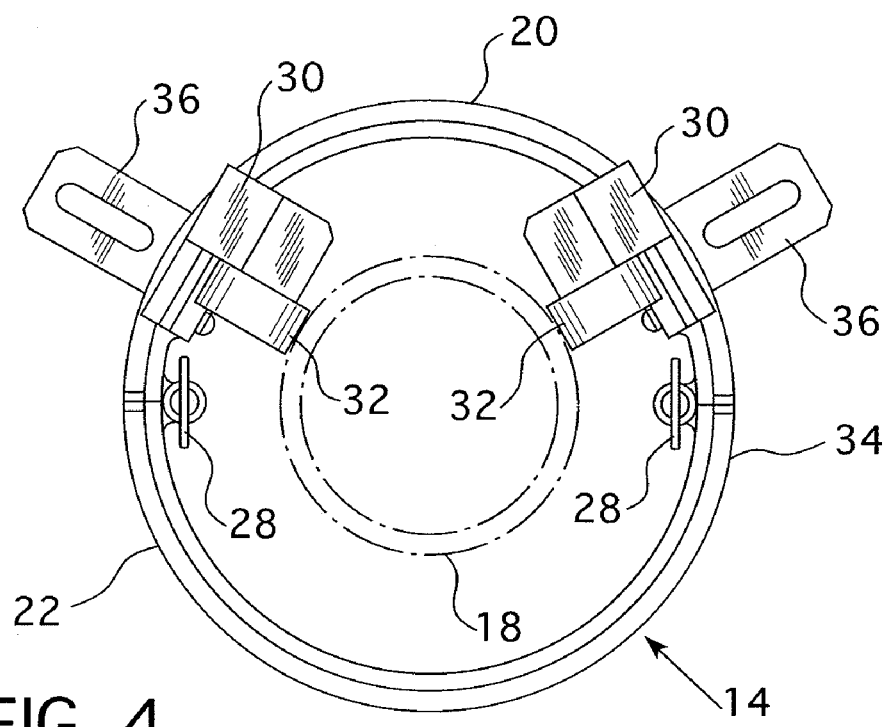
FIG. 4 is a front view of the collar assembly shown in FIG. 3.

The design of the collar can better be appreciated by reference to FIGS. 3 and 4. A different size collar is provided for each of the diameters of the pipes to be inspected. However, the design of each of the collars, aside from the differences in the dimensions, is the same. The collars are constructed in two separable halves 20 and 22 that are joined together by quick disconnect pins 28 that snap into sleeves at the collar seams that are formed from a center sleeve section 26 and two end sleeves sections 24. The end sleeve sections 24 are fixedly connected to one or the other of the upper or lower collar sections 20 and 22 and the central sleeve section 26 is fixedly connected to the other of the upper or lower collar sections 20 and 22. When the disconnect pins 28 are removed, the collar sections 20 and 22 can be separated and fit around the pipe. The quick disconnect pins 28 can then be placed within the sleeves formed by the sections 24 and 26 to fixedly attach the two halves of the collar 20 and 22 together around the pipe. The collar also includes at least two wheels 32 that are mounted on a bracket 30 that is attached to the inner wall of the collar 14. The wheels 32 maintain a space between the pipe 18 and the interior of the collar 14 that enables the scanner system 10 to negotiate angled piping. The collar 14 also includes at least two circumferentially spaced angle brackets 36 that are supported from the interior surface of the collar and extend out cantilevered off the rear of the collar 14 for attachment to an axial drive unit 12 that is shown in more detail in FIGS. 1, 2 and 5.

Figure 5:
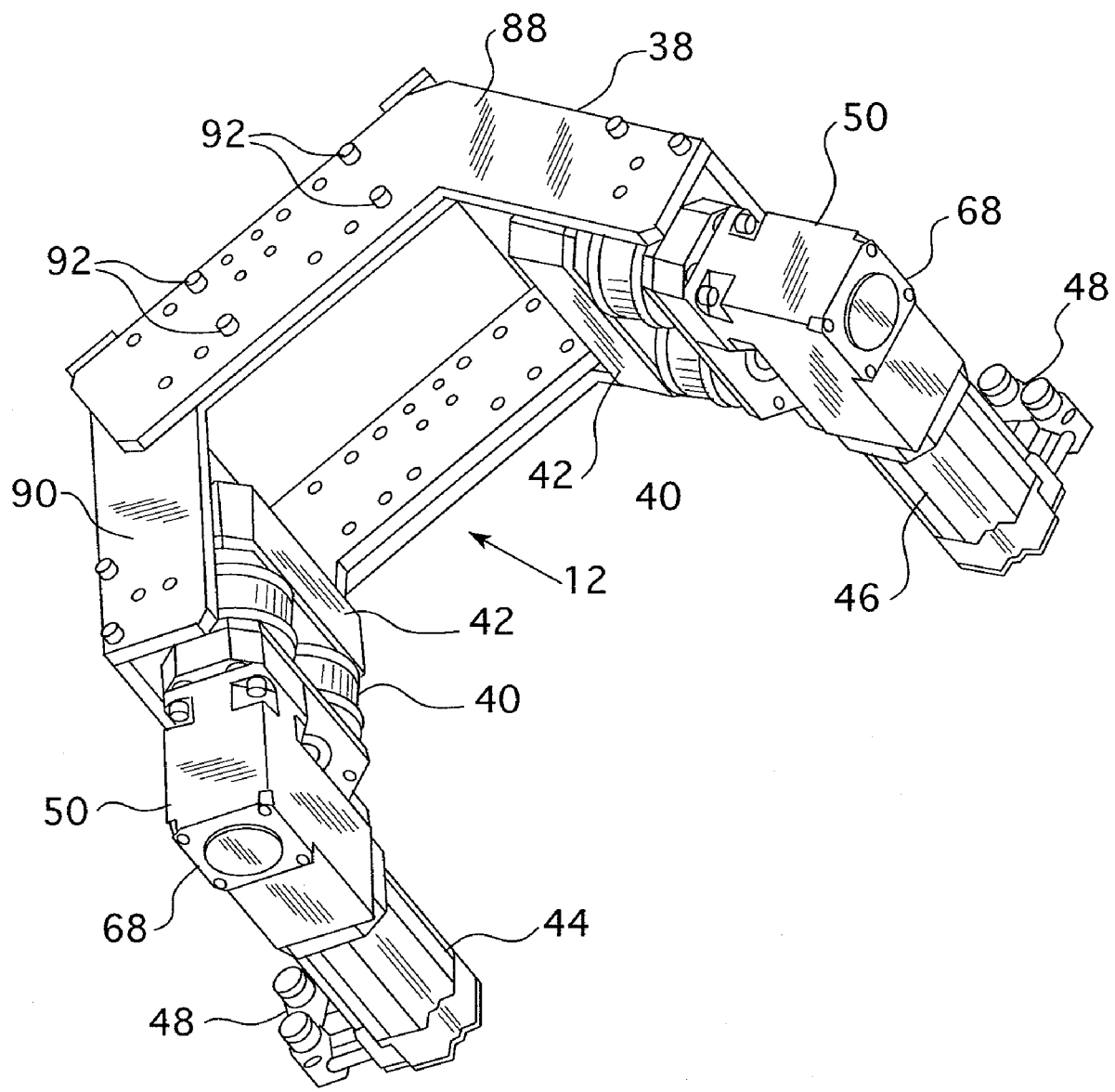
FIG. 5 is perspective view of one embodiment of the axial drive assembly of this invention.

The axial drive unit 12 has a support bracket that can best be observed from FIGS. 1 and 5, that is attached to the angled brackets 36 on the rear of the collar 14, as shown in FIG. 1. Each end of the support bracket 38 supports one of two brushless servo motors 44 and 46 which are controlled through control and feedback cabling connectors 48. The motors 44 and 46 power drive wheels 40 which are driven through a gear box 50 in a forward or reverse direction as directed by a programmed command signal that is communicated through the cabling connected to the control and feedback connectors 48. In the preferred embodiment, the drive wheels 40 are formed from a ferrous material that is magnetized by the magnets 42 supported by the support bracket 38 adjacent the drive wheels 40. The axial drive support bracket 38 is constructed in two sections 88 and 90 that overlap and are connected by the screws 92. The width of the overlapping sections can be adjusted by changing the holes that the screws 92 extend through to accommodate pipes of differing diameters. Accordingly, the axial drive unit 12 can propel the collar 14 in either a forward or reverse direction either continuously or in incremental steps over the distance between risers or vertical supports, all of which is preprogrammed and operates without operator intervention. Four drive wheels 40 are shown in the embodiment illustrated in FIGS. 2 and 5, though it should be appreciated that the number of drive wheels can be varied depending upon the application. The synchronization of the two motors 44 and 46 minimizes the ability of the scanner system 10 to corkscrew, i.e., spiral around the pipe as the scanner travels axially.

Figure 7:
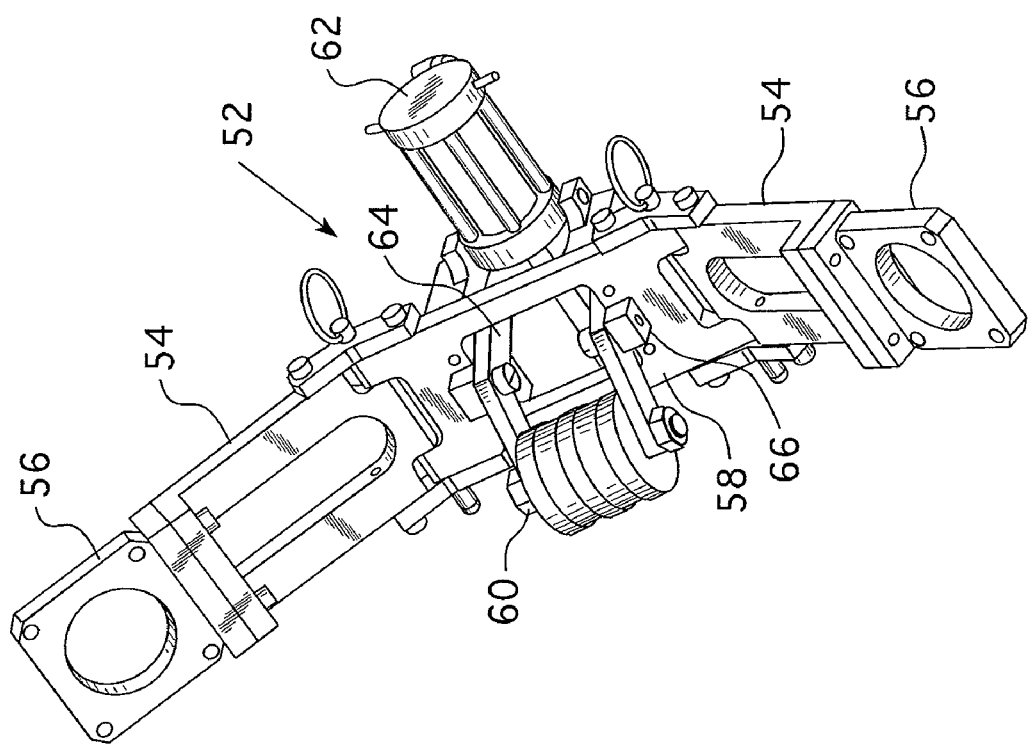
FIG. 7 is a perspective view of a second embodiment of the wheel support assembly which is designed to accommodate a different pipe diameter than the wheel support assembly illustrated in FIG. 6.
Figure 6:
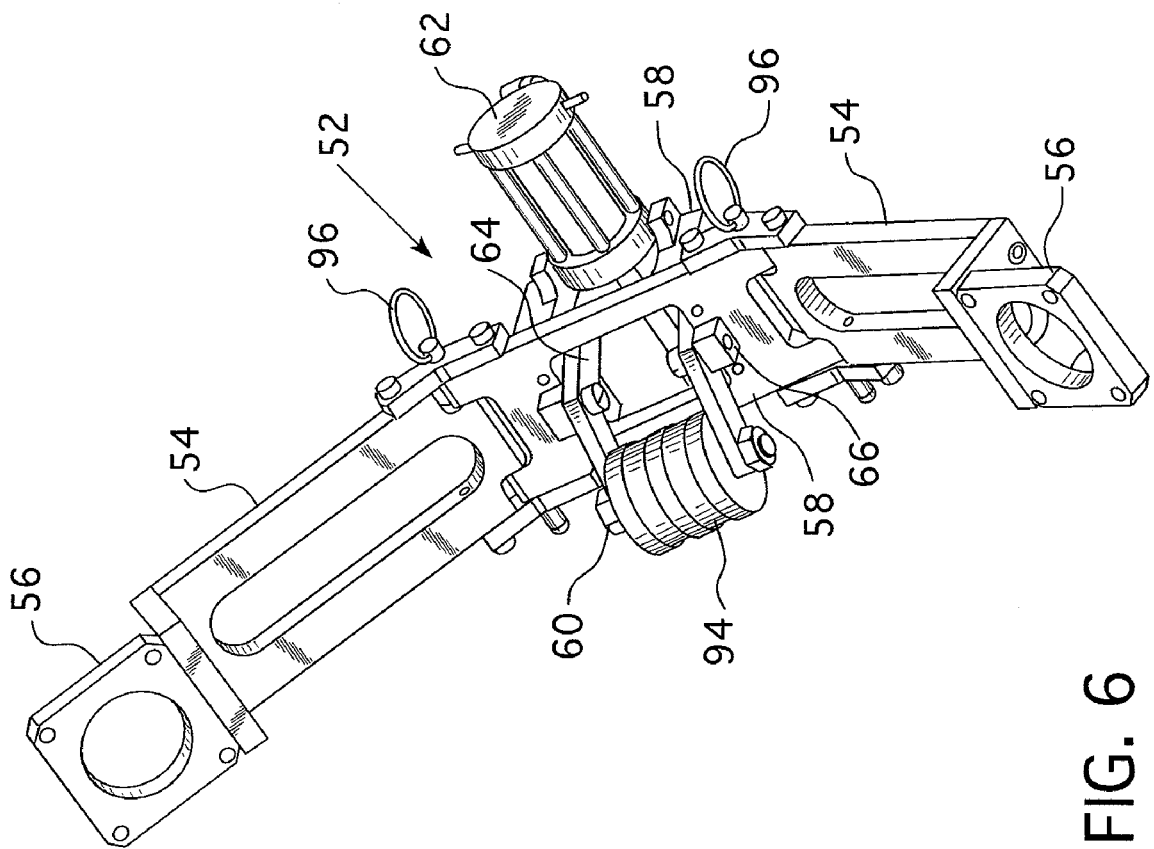
FIG. 6 is a perspective view of the underside of the wheel support assembly of this invention that can optionally be attached to the axial drive.
Figure 8:
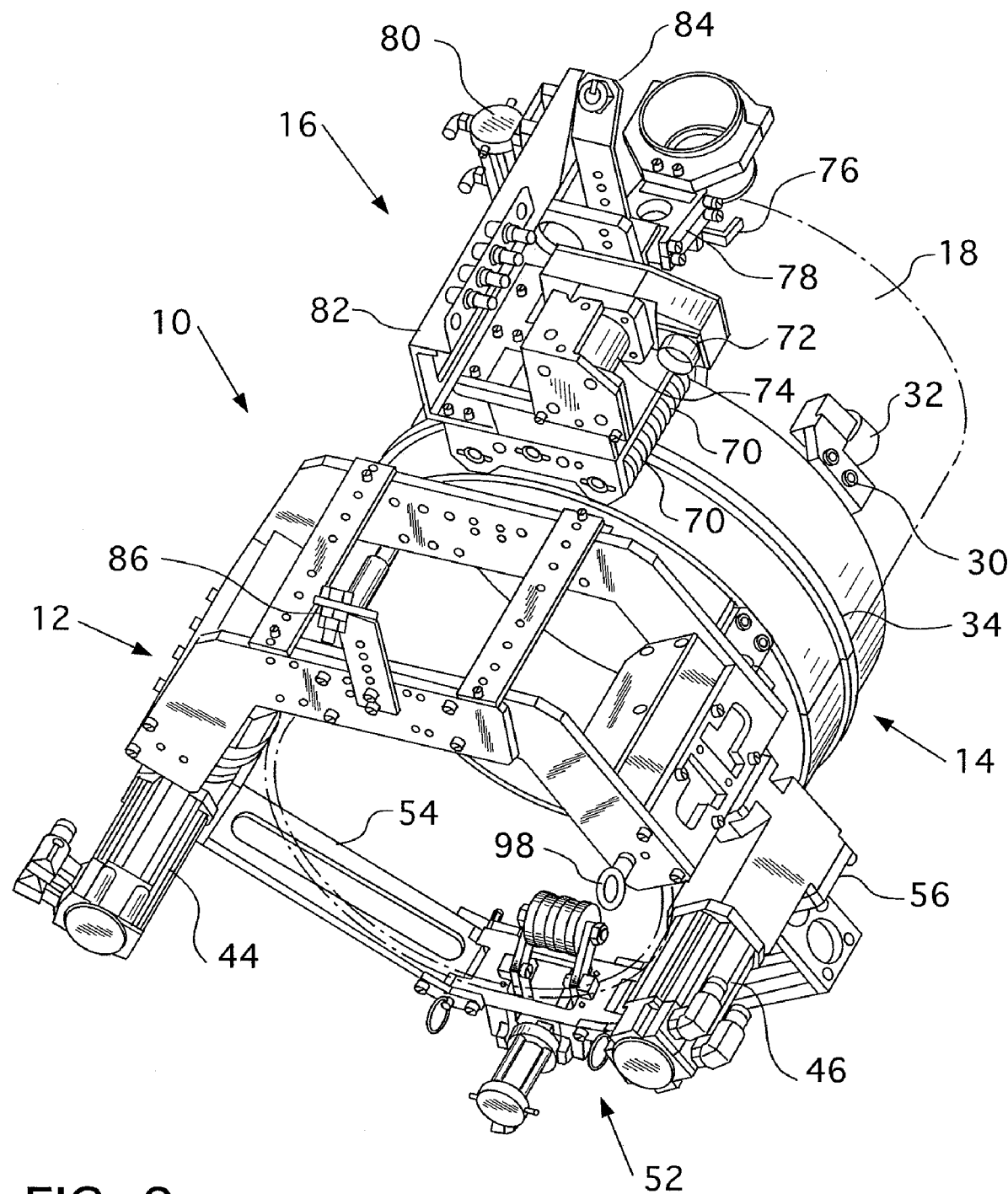
FIG. 8 is an isometric view of the pipe scanner of this invention with the wheel support assembly attached to the axial drive.

Optionally, to prevent corkscrewing on larger diameter pipes, a wheel support assembly 52 illustrated in FIG. 6 can be added. The wheel support assembly 52 has a central wheel housing 58 that supports a retractable wheel assembly 60 that is connected through linkages 64 about a pivot 66 to a pneumatic cylinder 62 that can raise or lower the wheel 94 into or out of contact with the surface of the pipe 18. Attachment arms 54 extend out on either side of the wheel housing 58 and have attachment brackets 56 connected to the distal ends of the attachment arms 54. The attachment arms 54 are connected to the wheel housing 58 with quick disconnect pins 96 for ease of removal. Using the quick disconnect pins 96, the attachment arms 54 and attachment brackets 56 may be exchanged for arms and brackets of a different configuration or size, such as shown in FIG. 7, to accommodate pipes of different diameters. The attachment brackets at the ends of the attachment arms 54 are connected to attachment brackets 68 on the gear boxes 50 as shown in FIG. 8. Also shown in FIG. 8 is an eyelet 98 which can be used for towing auxiliary inspection equipment.

The circumferential drive unit 16 is shown in FIGS. 1, 2 and 8 and runs on a raised track or rail 34 that extends radially outward from the outer surface of the collar 14. The track or rail 34 guides the circumferential drive 16 around the collar 14. Electrical control and communications cabling are connected to the electrical connector 72 which provides the power, control and communication for the motor 74 that drives at least one of the magnetized guide wheels 70 supported on either side of the front and rear of the underside of the circumferential drive unit 16. The guide wheels 70 have a central space that is designed to receive the track or rail 34 to guide the circumferential drive unit 16 around the collar 14. The collar 14 is desirably formed from a ferrous material so that the magnetic attraction between the collar and the magnetized guide wheels 70 maintain contact between the circumferential drive unit 16 and the collar 14 as the circumferential drive 16 travels completely around the collar 14, irrespective of the material the pipe is formed from. The circumferential drive unit 16 can be programmed to travel in a clockwise or counterclockwise direction either continuously or in incremental steps that enable it to traverse the full 360° circumference of the collar 14 while performing a complete scan. The programming of the circumferential drive unit 16 is completely independent of the programming of the axial drive unit 12 so that an infinite number of scan patterns can be developed to address most any situation. The circumferential drive unit 16 supports a cantilevered arm 82 that may be fixedly attached to the base of the circumferential drive unit 16 or connected through a servo four or six-way driven coupling that can provide fine control for positioning a nondestructive sensor connected to a bracket 76, a color TV camera 84 and a pipe cleaning brush 80, which are each supported by the arm 82. Additionally, a gimballed coupling 78 can be provided in between the cantilevered arm 82 and the sensor bracket 76 to facilitate positioning of the sensor. To facilitate unmanned scanning, the pipe system 10 includes forward and aft color cameras 84 and 86 and a pneumatically actuated pipe cleaning device 80. The pipe cleaning device is a steel brush that may be put in contact with the pipe surface by actuation of a pneumatic cylinder 80 which is shown in FIG. 8 supported at the distal end of the arm 82. The wire brush may then be driven along the pipe surface with the circumferential scanner. A servo driven coupling for the arm 82 may be used to scan an adjacent pipe up to a pipe riser and a portion of the riser itself.

Accordingly, the scanning system 10 of this invention is capable of scanning the 360° circumference of pipes of varying diameters over extended lengths without operator intervention. Furthermore, the scanning system of this invention can accomplish such scans at relatively high speeds over relatively short time spans to increase inspection throughputs.

While specific embodiments of the invention have been described in detail, it will be appreciated by those skilled in the art that various modifications and alternatives to those details could be developed in light of the overall teachings of the disclosure. For example, while a circumferentially continuous rail or track 34 is shown projecting radially outward from the collar 14, the rail 34 can be discontinuous or replaced with a grooved recess in the collar that a guide wheel on the circumferential drive carriage rides in. Furthermore, such a groove, or the rail, could have a radial contour that captures a portion of the guide wheel in a manner that maintains contact between the carriage drive wheels and the drive surface of the collar 14 as the circumferential drive unit encircles the collar 14. Further, the non-destructive sensor supported by the bracket 76 may be any sensor that can provide information about the condition of the wall of the pipe 18 that is surveyed, e.g., an ultrasonic sensor, an eddy current sensor, a video camera, an x-ray unit, etc. In addition, further drive configurations may be employed for either the axial drive unit or the circumferential drive unit. Accordingly, the particular embodiments disclosed are meant to be illustrative only and not limiting as to the scope of the invention which is to be given the full breath of the appended claims and any and all equivalents thereof.

What is claimed is:

1. A pipe scanner for nondestructively scanning an extended length of an outer circumference of a pipe along an axial dimension, comprising:
    a collar sized to fit around the outer circumference of the pipe with wheels supported by the collar oriented to travel axially on an outer surface of the pipe along the extended length;
    a track on an outer surface of the collar and extending circumferentially, substantially around the collar;
    a circumferential drive that rides on said track around an outer circumference of the collar;
    a nondestructive sensor supported on the circumferential drive, for monitoring the surface of the pipe; and
    an axial drive connected to the collar, having a drive surface that rides on the outer surface of the pipe for moving the collar along the extended length.

2. The pipe scanner of claim 1 wherein the drive surface of the axial drive is at least one wheel.

3. The pipe scanner of claim 2 wherein the at least one wheel of the drive surface of the axial drive is magnetized.

4. The pipe scanner of claim 2 wherein the drive surface of the axial drive is at least two wheels with each wheel being spaced from the other around the circumference of the pipe.

5. The pipe scanner of claim 1 wherein the axial drive has at least two drive surfaces that are circumferentially spaced from each other and a first motor for operating a first of the drive surfaces and a second motor for operating a second of the drive surfaces, wherein the first and second motors are synchronized.

6. The pipe scanner of claim 5 including a wheel support assembly attached at one end to the first motor and at a second end around the pipe to the second motor with an idler wheel extending off the wheel support assembly toward the pipe substantially midway between said first and second motors.

7. The pipe scanner of claim 6 including means for moving the idler wheel relative to the wheel support assembly towards and away from the pipe.

8. The pipe scanner of claim 6 wherein the wheel support assembly includes a wheel housing, attachment arms that extend out on either side of the wheel housing and attachment brackets that extend from the distal end of the attachment arms, wherein the attachment arms are coupled to the wheel housing with a quick disconnect so the attachment arms can easily be interchanged with attachment arms of another configuration to accommodate different diameter piping.

9. The pipe scanner of claim 1 wherein the circumferential drive can travel 360 degrees or more around the outer circumference of the collar.

10. The pipe scanner of claim 9 wherein the circumferential drive can travel in either a forward or a reverse circumferential direction.

11. The pipe scanner of claim 1 wherein the distance the axial drive moves the collar, the direction of such moves and the timing of such moves are programmable.

12. The pipe scanner of claim 11 wherein the distance the circumferential drive moves around the circumference, the direction of such moves and the timing of such moves are programmable.

13. The pipe scanner of claim 12 wherein the programming of the circumferential drive is independent of the programming of the axial drive.

14. The pipe scanner of claim 1 including an adjustable coupling between the nondestructive sensor and the circumferential drive that can change an orientation of the nondestructive sensor.

15. The pipe scanner of claim 1, wherein the wheels supported by the collar maintain a space between an interior of the collar and the outer surface of the pipe.

16. The pipe scanner of claim 15 wherein the space between the interior of the collar and the outer surface of the pipe is sufficient to accommodate angled pipe runs.

17. The pipe scanner of claim 1 wherein the track comprises a raised rib on the collar that extends substantially continuously, circumferentially around the collar.

18. The pipe scanner of claim 17 wherein the circumferential drive includes at least two wheels oriented to run circumferentially and spaced from each other to receive the rib therebetween.

19. The pipe scanner of claim 1 including a support arm that is cantilevered off of the circumferential drive and supports the sensor over the pipe with the support arm attached to the circumferential drive through a servo driven coupling.

* * * * *